United States Patent
Blumenthal et al.

(10) Patent No.: US 6,653,522 B1
(45) Date of Patent: Nov. 25, 2003

(54) HOT MELT ADHESIVES BASED ON SULFONATED POLYESTERS COMPRISING WETNESS INDICATOR

(75) Inventors: Mitchell J. Blumenthal, Belle Mead, NJ (US); Charles W. Paul, Madison, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/289,781

(22) Filed: Apr. 9, 1999

(51) Int. Cl.[7] ................................. A61F 13/15
(52) U.S. Cl. ................... 604/361; 604/389; 524/275; 524/320; 524/603
(58) Field of Search .................... 604/361, 358, 604/389; 524/186, 221, 227, 230, 488, 275, 320–322, 190, 288, 603, 297, 270–271

(56) References Cited

U.S. PATENT DOCUMENTS

| | | |
|---|---|---|
| 4,052,368 A | 10/1977 | Larson |
| 4,073,777 A | 2/1978 | O'Neill et al. |
| 4,231,370 A | 11/1980 | Mroz et al. |
| 4,233,196 A | 11/1980 | Sublett |
| 4,257,928 A | 3/1981 | Vachon et al. |
| 4,304,901 A | 12/1981 | O'Neill et al. |
| 4,525,524 A | 6/1985 | Tung et al. |
| 4,575,525 A | 3/1986 | Wacome et al. |
| 4,598,142 A | 7/1986 | Hilbert et al. |
| 4,678,824 A | 7/1987 | Lauria |
| 4,681,576 A | 7/1987 | Colon et al. |
| 4,735,843 A | 4/1988 | Noda |
| 4,743,238 A | 5/1988 | Colon et al. |
| 4,895,567 A | 1/1990 | Colon et al. |
| 4,910,292 A | 3/1990 | Blount |
| 4,973,656 A | 11/1990 | Blount |
| 4,990,593 A | 2/1991 | Blount |
| 5,035,691 A | 7/1991 | Zimmel et al. |
| 5,066,711 A | 11/1991 | Colon et al. |
| 5,089,548 A | 2/1992 | Zimmel et al. |
| 5,098,962 A | 3/1992 | Bozich |
| 5,296,535 A | 3/1994 | Nesiewicz et al. |
| 5,342,861 A | 8/1994 | Raykovitz |
| 5,356,963 A | 10/1994 | Kauffman et al. |
| 5,360,845 A | 11/1994 | Billmers et al. |
| 5,382,652 A | 1/1995 | Fukuda et al. |
| 5,387,623 A | 2/1995 | Ryan et al. |
| 5,532,306 A | 7/1996 | Kauffman et al. |
| 5,543,488 A | 8/1996 | Miller et al. |
| 5,552,411 A | 9/1996 | Downing et al. |
| 5,552,495 A | 9/1996 | Miller et al. |
| 5,571,876 A | 11/1996 | Miller et al. |
| 5,574,076 A | 11/1996 | Sharak et al. |
| 5,583,187 A | 12/1996 | Sharak et al. |
| 5,605,764 A | 2/1997 | Miller et al. |
| 5,718,790 A | 2/1998 | Miller et al. |
| 5,750,605 A | 5/1998 | Blumenthal et al. |

FOREIGN PATENT DOCUMENTS

| | | |
|---|---|---|
| WO | WO 95/05413 | 2/1995 |
| WO | WO 95/18191 | 7/1995 |
| WO | WO 96/07540 | 3/1996 |

*Primary Examiner*—Weilun Lo
(74) *Attorney, Agent, or Firm*—Cynthia L. Foulke

(57) ABSTRACT

A wetness indicating hot melt adhesive composition comprising a pH adjusting component and an indicating agent which is capable of changing color in response to changes in pH. The adhesive composition may comprise 20 to 80% by weight of a sulfonated polyester, 3 to 30% by weight of an acidic plasticizer and 0.05 to 3% by weight of an indicator.

12 Claims, No Drawings

HOT MELT ADHESIVES BASED ON SULFONATED POLYESTERS COMPRISING WETNESS INDICATOR

BACKGROUND OF THE INVENTION

Hot melt adhesives, 100% solids materials, which are applied to a substrate when molten and cooled to harden the adhesive layer, are used commercially for a wide variety of applications. The major advantage of hot melt adhesive systems is the lack of a carrier fluid which eliminates the need for drying the adhesive film once it is applied to the substrate. This elimination of the drying step overcomes hazards associated with solvent usage and also allows for faster production line speeds and lower transportation costs.

For various applications, it is also desired that some hot melt adhesives be hydrophilic, i.e., be water-soluble, water-sensitive or water-activated. Such hydrophilic adhesives find use, for example, in moisture activated envelope adhesives and in the construction of flushable disposable products including diapers and sanitary napkins where they promote the disintegration of the disposable article in water.

Hot melt adhesives have historically been based on petroleum derived polymers such as polyethylene, ethylene-vinyl acetate, styrenic block copolymers and polypropylene. Water sensitive hot melts have also been prepared from vinyl pyrrolidone polymers including vinyl acetate/vinyl pyrrolidone copolymers. All these adhesive compositions are further tackified, plasticized and/or reinforced with a variety of resins, oils and/or waxes which are derived from both petroleum and naturally occurring feedstocks such as wood, gum and tall oil rosin and terpenes.

In the production of disposable articles, hot melt adhesives are typically extruded at elevated temperatures (about 250° F. to 350° F.) directly onto a work piece, typically a polyethylene or polypropylene film, a nonwoven fabric, an absorbent material, a tissue, or a film which can then be bonded to another nonwoven fabric, absorbent material, tissue, or film using the hot melt adhesive. Application of the adhesive may be extruded by fine line, multi-dot, multi-line methods or spray techniques. The hot melt adhesive is used to laminate layers or attach elastic, particularly for waist or leg band closures for disposable diapers.

In such disposable products, it is desirable to know if the product has become wet with water or urine. For example, it may not be readily apparent that a diaper has become wet due to the plastic coating or water proof panty worn over the diaper.

SUMMARY OF THE INVENTION

Accordingly, the present invention is directed to a hot melt adhesive composition which is capable of indicating the presence of water or urine therein and to disposable products comprising such adhesives. Specifically, the hot melt adhesives of the present invention change color in response to water or urine.

The hot melt adhesives of the present invention comprise a pH adjusting component and an indicating agent which is capable of changing color in response to changes in pH.

DETAILED DESCRIPTION OF THE INVENTION

The adhesives of the present invention comprise a pH adjusting component and an indicating agent which is capable of changing color in response to changes in pH.

The indicating agent is a component which is capable of changing color in response to changes in pH. Acid-base indicators are preferred because they change color rapidly. The most preferred indicating agents are those which change to a bright, vivid color. The acid-base indicators for use herein are those which change color at a pH in the range of about 3 to 7, such as Ethyl Red, Bromophenol Blue (made by Eastman Kodak), Bromocresol Green mixed with Bromophenol Blue, or Bromophenol Blue. Most preferred is Bromocresol Green which changes color in the range pH 3.8 to 5.4.

The indicating agent is used in an amount effective to provide the composition with a readily visible color when the composition exposed to water or urine; generally about 0.05 to 0.1 weight percent indicator, based on the weight of the composition. Preferably, the indicating agent is present in amounts of 0.005 to 3% by weight of the adhesive composition.

The adhesives of the present invention also comprise a pH adjusting agent which is an acidic or basic component which changes the pH of the hot melt adhesive. Preferred are acidic plasticizers which have an acidic functional end group, such as a carboxylic acid. Examples of such acidic plasticizers include isostearic acid, azelaic acid, stearic acid, oleic acid, linoleic acid, ricinoleic acid and dimer acid. Isostearic acid is preferred.

The acid plasticizer is used to render the resulting adhesive acidic. As used herein, acidic is defined as a pH less than the indicating range of the indicating agent. The adhesives described herein, without the acidic plasticizer, are of a pH such that the addition of Bromocresol Green (or any indicating agent) to the adhesive causes the indicator to change. Therefore, it was found in accordance with the present invention, that the addition of an acidic plasticizer adjusts the pH of the adhesive to below the activation range of the indicating agent, preventing the indicating agent from changing color unless exposed to a substance that will raise the pH, such as water or urine, as will be described below.

Specifically, the addition of urine, which has a pH is the range 5.8 to 7.4, or the addition of water with a pH of 7, to the adhesive, causes the pH of the adhesive to increase, passing through the indicator range, causing a color change signaling that the adhesive is wet with water or urine. The pH range of urine is disclosed in J. L. Hammone, et al. TAPPI Int. Dissolving Pulps Conf. (Geneva) Proc.: 247–264 (Mar. 24–27, 1987).

Any indicating agent capable of changing color in response to a change in pH may be used. Therefore when formulating an adhesive in accordance with the present invention, the acidic plasticizer and indicating agent are chosen so that the pH of the adhesive is such that when urine or water are added, the pH changes in such a way that the indicator is activated.

The pH adjusting agent and indicating agent are formulated into an adhesive composition. Any base polymer for hot melt adhesives may be used such as polyethylene, ethylene-vinyl acetate, styrenic block copolymers, polypropylene, and vinyl pyrrolidone polymers including vinyl acetate/vinyl pyrrolidone copolymers. Preferably the base polymer is a sulfonated polyester. In this embodiment, the present invention is directed to hot melt adhesive compositions comprising (a) 20 to 80% by weight of a sulfonated polyester; (b) 3 to 30% by weight of a pH adjusting agent, particularly an acidic plasticizer; and (c) to 0.05 to 3% by weight of an indicating agent capable of changing color in response to changes in pH.

The major component of the adhesive of the invention, present in an amount of 20 to 80% by weight of the adhesive, is a sulfonated polyester condensation polymer comprising the reaction product of:

(a) at least one difunctional dicarboxylic acid or corresponding methyl ester which is not a sulphomonomer;

(b) 2 to 25 mole percent of at least one sulphomonomer containing at least one metallic sulfonate group or nitrogen-containing non-metallic sulfonate group attached to an aromatic or cycloaliphatic nucleus and at least one functional group selected from the group consisting of hydroxyl, carboxyl, and amino;

(c) at least one difunctional reactant selected from a glycol or a mixture of a glycol and diamine having two —NRH groups, the glycol containing two —C($R^1$)$_2$—OH groups wherein R in the reactant is hydrogen or an alkyl group of 1 to 6 carbon atoms, and $R^1$ in the reactant is a hydrogen atom, an alkyl of 1 to 5 carbon atoms, or an aryl group of 6 to 10 carbons atoms;

(d) 0 to 40 mole percent of a difunctional reactant selected from hydroxycarboxylic acids having one —C(R)$_2$—OH group, aminocarboxylic acids having one —NRH group, amino-alcohols having one —C(R)$_2$—OH group and one —NRH group, or mixtures of said difunctional reactants wherein R in the reactant is hydrogen or an alkyl group of 1 to 6 carbon atoms; and (e) 0 to 40 mole percent of a multifunctional reactant containing at least three functional groups selected from hydroxyl, carboxyl, and mixtures thereof wherein at least a portion of the multifunctional reactant contains at least three hydroxyl groups, wherein all stated mole percentages are based on the total of all acid, hydroxyl and amino group containing reactants being equal to 200 mole percent, and wherein the polymer contains proportions of acid-group containing reactants (100 mole percent acid) to hydroxy- and amino-group containing reactants (100 mole percent base) such that the value of (equivalents) EQ (base) divided by (equivalents) EQ (acid) is between 0.5 and 2.

The difunctional acid or ester reactant of (a) of the composition of the present invention is preferably substantially aliphatic in nature and may be an acid selected from the group consisting of oxalic; malonic; dimethylmalonic; succinic; glutaric; adipic; trimethyladipic; pimelic; pivalic; fumaric; maleic; dodecanoic; 2,2-dimethylglutaric; azelaic; sebacic; 1,3-cyclopentane-dicarboxylic; 1,2-cyclohexanedicarboxylic; 1,3-cyclohexane dicarboxylic; 1,4-cyclo-hexanedicarboxylic; phthalic; terephthalic; isophthalic; 2,5-norbornane-dicarboxylic; 1,3-naphthalic; diphenic; 4,4'-oxydibenzoic; diglycolic; thiodipropionic; 4,4'-sulfonyldibenzoic; and 2,5-naphthalenedicarboxylic acids and esters thereof and mixtures thereof. The difunctional dicarboxylic acid or ester reactant of (a) is preferably selected from the group of acids consisting of isophthalic acid, terephthalic acid, phthalic anhydride (acid), adipic acid, pivalic acid, dodecanedioic acid, sebacic acid, azelaic acid, 1,4-cyclohexanedicarboxylic acid, 1,3-cyclohexanedicarboxylic acid, maleic anhydride, fumaric acid, succinic anhydride (acid), 2,6-naphthalenedicarboxylic acid, and glutaric acid and esters thereof and mixtures thereof. The more preferred difunctional dicarboxylic acid reactants of (a) are selected from the group consisting of isophthalic acid, adipic acid, 1,4-cyclohexanedicarboxylic acid, 1,3-cyclohexanedicarboxylic acid and mixtures thereof with 1,4-cyclohexanedicarboxylic acid being most preferred.

The sulphomonomer reactant of (b) is preferably selected from the group consisting of difunctional monomers containing a —SO$_3$M group attached to a nucleus selected from the group consisting of benzene, naphthalene, anthracene, diphenyl, oxydiphenyl, sulfonyldiphenyl, and methylenediphenyl, wherein M is Na+, Li+, Mg++, Ca++, Fe++, and Fe+++. The more preferred sulfomonomer reactant of (b) is selected from the group consisting of diols an diol adducts of multifunctional reactant containing at least three hydroxyl groups and a monocarboxylic acid sulfomonomer containing at least one metallic sulfonate group or nitrogen-containing non-metallic sulfonate group attached to an aromatic or cyclo-aliphatic nucleus. Alternatively, a more preferred group of sulfomonomers include 5-sodiosulfoisophthalic acid, dimethyl 5-sodiosulfoisophthalate, 5-lithiosulfoispthalic acid, and bis(2-hydroxyethyl)-5-sodiosulfoisophthalate; with the 5-sodiosulfoisophthalic acid or dimethyl 5-sodiosulfoisophthalate being most preferred.

The difunctional reactant of (c) is preferably a diol selected from the group consisting of ethylene glycol; propylene glycol, 1,3-propanediol, 2-methyl-1,3-propanediol, 2,4-dimethyl-2-ethyl-hexane-1,3-diol, 2,2-dimethyl-1,3-propanediol (neopentyl glycol), 2-ethyl-2-butyl-1,3-propanediol (neopentyl glycol), 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl-1,6-hexanediol, thiodiethanol, 1,2-cyclohexanedimethanol, 1,3-cyclohexanedimethanol, 1,4-cyclohexanedimethanol, 2,2,4,4-tetramethyl-1,3-cyclobutanediol, p-xylylenediol,diethylene glycol, triethylene glycol, tetraethylene glycol, pentaethylene glycol, hexaethylene glycol, heptaethylene glycol, octaethylene glycol, nonaethylene glycol, decaethylene glycols, 2,2,4-trimethyl-1-1,3-pentanediol, hydroxypivalyl hydroxypivalate, dipropylene glycol, 1,10-decanediol, hydrogenated bisphenol A, and mixtures thereof. The difunctional reactant of (c) is more preferably selected from the group consisting of diethylene glycol; neopentyl glycol, cyclohexanedimethanol, 2-ethyl-2-butyl-1,3-propanediol, 2,2,4-trimethyl-1,3-pentanediol, hydroxypivalyl hydroxypivalate, and 2-methyl-1,3-propanediol, with diethylene glycol, neopentyl glycol, and cyclohexanedimethanol being most preferred.

Advantageous difunctional components which are aminoalcohols include aromatic, aliphatic, heterocyclic and other types as in regard to component (d). Specific examples include 5-aminomethyl-cyclohexanemethanol; 5-amino-2-ethyl-pentanol-1, 2-(4-b-hydroxyethoxy-phenyl)-1-aminoethane, 3-amino-2,2-dimethylpropanol, hydroxyethylamine, etc. Generally these aminoalcohols contain from 2 to 20 carbon atoms, one —NRH group and one —C(R)$_2$—OH group.

Advantageous difunctional monomer components which are aminocarboxylic acids include aromatic aliphatic, heterocylic, and other types as in regard to component (d) and include lactams. Specific examples include 6-aminocaproic acid, its lactam known as caprolactam, omega-aminoundecanoic acid, 3-amino-2-dimethylpropionic acid, 4-(b-aminoethyl)-benzoic acid, 2-(b-aminopropoxy) benzoic acid, 4-aminomethlcyclohexanecarboxylic acid, 2-(b-aminopropoxy) cyclohexanecarboxylic acid, etc. Generally these compounds contain from 2 to 20 carbon atoms.

Advantageous examples of difunctional monomer component (d) which are diamines include ethylene-diamine; hexamethylenediamine; 2,2,4-trimethylhexamethylenediamine; 4-oxaheptane-1,7-diamine; 4,7-dioxadecane-1,10-diamine; 1,4- cyclohexanebismethylamine; 1,3-cycloheptamethylenediamine; dodecamethylenediamine, etc.

Reactant (e), when used, preferably contains 3 to 6 hydroxyl and/or carboxyl groups; more preferred is trimethylolpropane (TMP), trimethylolethane (TME), glycerine, pentaerythritol, arytritol, threitol, dipentaerythritol, sorbitol, trimellitic anhydride, pyromellitic dianhydride, or dimethylolpropionic acid, with TMP being most preferred. It is preferred that reactant (e) be present in a minor amount up to 40 mole percent, more preferred 0 to 20 mole percent.

The polyester composition used as a component of the hot melt adhesives of the present invention preferably comprises 60 to 100 mole percent of (a), 4 to 20 mole percent of (b), 80 to 100 mole percent of (c), 0 to 10 mole percent of (d), and 0 to 20 mole percent of (e).

In other more preferred embodiments of the invention the polyester comprises 60 to 100 mole percent of 1,4-cyclohexanedicarboxylic acid; 4 to 20 mole percent of 5-sodiosulfoisophthalic acid or dimethyl 5-sodiosulfoisophthalate; and 80 to 100 mole percent of diethylene glycol, neopentyl glycol or cyclohexanedimethanol.

The preparation of the polyesters used herein is generally described, for example, in U.S. Pat. Nos. 4,910,292, 4,973,656, and 4,990,593.

The preferred polycondensation reactant conditions for the preparation of the polyester are at a temperature of 150 to 230° C. in the presence of a catalyst. The catalyst for the polycondensation reaction is preferably an acid catalyst more preferably an organo-metallic compound, such as a tin or titanium containing compound. Suitable examples of the acid catalyst include dibutyltinoxide, stannous oxalate, titaniumtetraisopropoxide, butylstannoic acid, and p-toluenesulfonic acid, with butylstannoic acid being most preferred. A preferred butylstannoic acid catalytic amount is 0 to 0.5 weight percent, based on the total weight of reactants, preferably 0.01 to 0.2 weight percent, with 0.1 weight percent being most preferred.

The viscosity of the polyester is preferably between 1000 cP and 1,000,000 cP at 350° F., most preferably between 5000 and 60,000 cP. Viscosity is measured in a Brookfield viscometer using a #27 spindle. Viscosity is generally related to molecular weight with higher viscosities corresponding to higher molecular weights.

The adhesive compositions of the present invention may also comprise additional optional components such as polar nonionic, cationic and anionic plasticizers; tackifiers; crystalline materials; and stabilizers.

Depending on the end-use application, various compatible nonionic liquid plasticizers or extending oils may optionally be present in the composition. Preferred compatible plasticizers are non-crystalline in nature and include polar liquid plasticizers including phthalate plasticizers such as dioctyl phthalate and butyl benzyl phthalate (e.g., SANTICIZER 160 from Monsanto); liquid polyesters (non-crystalline) such as DYNACOL 720 from Hüls and the liquid polymeric plasticizer available from C. P. Hall; benzoate plasticizers such as 1,4-cyclohexane dimethanol dibenzoate (e.g., BENZOFLEX 352 available commercially from Velsicol), diethylene glycol/dipropylene glycol dibenzoate (e.g., BENZOFLEX 50 from Velsicol) and diethylene glycol dibenzoate where the mole fraction of hydroxyl groups which have been esterified ranges from 0.5 to 0.95 (e.g., BENZOFLEX 245 HIGH HYDROXYL also from Velsicol); phosphate plasticizers such as t-butylphenyl diphenyl phosphate (e.g., SANTICIZER 154 available commercially from Monsanto); poly (ethylene glycol) with molecular weight below about 1000 and derivatives of poly(ethylene glycol) (e.g., PYCAL 94, the phenyl ether of PEG, available commercially from ICI); ethoxylated bis phenol A (e.g., MACOL 206 EM from PPG Industries); dinonyl phenol ethyoxylates (e.g., SURFONIC DNP 100 from Huntsman Chemical Corp.); liquid rosin derivatives having Ring and Ball melting points below about 60° C. such as the methyl ester of hydrogenated rosin (e.g., HERCOLYN D from Hercules); as well as vegetable and animal oils such as glycerol esters of fatty acids and polymerization products thereof. Particularly preferred plasticizer include phenyl ether of polyethylene-glycol; butyl benzyl phthalate; benzoates such as 1,4-cyclohexane dimethanol dibenzoate, diethylene glycol/dipropylene glycol dibenzoate, and diethylene glycol dibenzoate where the mole fraction of hydroxyl groups which have been esterified ranges from 0.5 to 0.95. These plasticizers are also polar in chemical composition and show improved compatibility over plasticizers which are not polar such as Mineral Oil.

Examples of cationic plasticizers include the fatty amine quaternary ammonium salts, such as ATLAS G-265 with HLB of 33, available from ICI; and ATLAS-G-3634A an imidazoline quaternary ammonium salt, also available from ICI.

Anionic plasticizers suitable for use herein are available in either solid or liquid form. When present, the adhesive composition will comprise 1 to 30% of anionic plasticizers. Examples of anionic plasticizers include the sulfosuccinate salts, such as sodium dioctyl sulfosuccinate, a solid plasticizer available under the tradename CYTEC OT-100 from Cytec Industries; sulfated fatty acids such as AHCOWET RS from ICI; and EMULSIFIER K-30, a solid alkane sulfonate available from Bayer Inc. Preferred is EMULSIFIER K-30. It has been found, in accordance with the present invention, that the anionic plasticizer will accelerate the color change of the indicating agent.

The compatible tackifying resins useful in the adhesive compositions are generally polar in nature and have a Ring and Ball softening point greater than 60° C. and include rosin and rosin derivatives, pure phenolic resins, and the like. More particularly, the useful tackifying resins include any compatible resins or mixtures thereof such as (1) natural and modified rosins such, for example, as gum rosin, wood rosin, tall oil rosin, distilled rosin, hydrogenated rosin, dimerized rosin, and polymerized rosin; (2) rosin esters such as glycerol and pentaerythritol esters of natural and modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; and (3) phenolic modified α-methyl styrene resins as well as the hydrogenated derivatives thereof. Mixtures of two or more of the above described tackifying resins, as well as blends of the above resins with small amounts of (e.g., less than about 20% of the adhesive) less compatible resins may be utilized for some formulations.

Representative polar tackifiers include ionic materials such as FORAL NC available from Hercules; non-ionic materials such as FORAL AX also from Hercules; alpha methyl styrene phenolics such as URATAK 68520 from DSM Resins, and rosin esters such as UNITAC R100L available from Union Camp. The preferred tackifier for use herein is FORAL NC.

Another tackifier is sucrose benzoate which is particularly useful due to its biodegradable and compostable character. Sucrose benzoate is preferably utilized in its alcohol soluble form wherein the sucrose is partially esterified. This grade is a light colored, clear non-crystalline solid with a softening point of about 95° C. Alternatively, the non-alcohol organic soluble grade, a water-clear, non-crystalline flake solid having a softening point of 98° C. may also be used. Both grades are available commercially from Veliscol Chemical Corporation.

High polarity hydroxyl-containing tackifiers are most preferred. Among these are styrene allyl alcohol copolymers available from ARCO Chemical under the tradename SAA-100, and orthophthalate neopentyl glycol polyester polyol available from Stepan under the tradename Stepanol PN-110.

Additionally, small amounts (i.e., less than 20 percent by weight) of non-polar tackifiers may be used in combination with the previously described tackifiers. Typical of this class of non-polar tackifiers are the aromatic/aliphatics such as ECR-149B from Exxon Chemical; aromatics such as KRISTALEX 3085 from Hercules; aliphatic hydrocarbons such as WINGTAC 95 from Goodyear; and cyclic aliphatics such as EASTOTAC H-100 from Eastman Chemical.

While the tackifier may comprise up to about 50% of the adhesive, it is generally used in amounts of about 0 to 35% by weight.

The adhesives of the invention may also comprise at least one crystalline wax material selected from the group consisting of a compatible crystalline wax diluent and a crystalline thermoplastic polymer. The crystalline wax materials are employed at levels of about 5 to 40% by weight by weight to reduce the melt viscosity while improving heat resistance. The waxes used must be highly polar, containing $\geq 3 \times 10^{-3}$ equiv/g of polar groups and at least one group per molecule and with a molecular weight below 500 g/mole. Higher concentrations of polar groups are necessary for higher molecular weight waxes. These polar groups include hydroxyl, amide (primary, secondary, and tertiary), sulfone, phosphate esters, sulfonamide, carbonate, urea, amine, urethane, carboxylic acid; and carboxylate salts, ureas, and sulfonate salts.

Suitable crystalline polar waxes include 12-hydroxystearamide, N-(2-hydroxy ethyl) 12-hydroxystearamide (PARICIN 220 from CasChem), stearamide (KEMAMIDE S from Witco), glycerin monostearate, sorbitan monostearate, and 12-hydroxy stearic acid. Also useful in combination with the above are the less polar waxes such as N,N'-ethylene-bis-stearamide (KEMAMIDE W-40 from Witco), hydrogenated castor oil (castor wax), oxidized synthetic waxes, and functionalized synthetic waxes such as oxidized polyethylene waxes (PETROLITE E-1040).

The adhesives of the invention may comprise a crystalline component which may alternatively be a crystalline hydrophobic thermoplastic polymer present in the adhesive 5 to 60%, preferably 5 to 40%. These polymers are employed in order to impart flexibility, toughness and strength. Suitable crystalline thermoplastic polymers include ethylene vinyl acetate copolymers containing about 12 to 50% vinyl acetate, ethylene acrylic acid, ethylene methyl acrylate and ethylene n-butyl acrylate copolymers as well as polylactide, caprolactone polymers and poly(hydroxy-butyrate/hydroxyvalerate), polyvinyl alcohol, linear saturated polyesters such as DYNAPOL or DYNACOLL polymers from H üls, or GRILTEX from EMS-Chemie, poly (ethylene oxide) polyether amide or polyester ether block copolymers available from Atochem (PEBAX) or Hoechst Celanese (RITEFLEX) respectively, and polyamide polymers such as those available from Union Camp (UNIREZ) or Hüls (VESTAMELT). The polymers added may be amorphous or crystalline, but at least 5% of a crystalline polymer is required to achieve adequate properties.

Preferred among these crystalline polymers are other polyester polymers such as those available from EMS-Chemie, Sumter, S.C., under the tradename GRILTEX, or from Hüls America, Piscataway, N.J., under the tradenames DYNAPOL and DYNACOLL (lower molecular weight). Also preferred are polyamides such as those available from Union Camp, Wayne, N.J., under the UNIREZ tradename or copolyamides available from Hüls under the VESTAMELT tradename and also from EMS-Chemie also under the GRILTEX name.

It may also be desirable to incorporate into the hot melt adhesive up to 20% by weight of certain other hydrophilic non-crystalline polymers such as hydroxyethyl cellulose, hydroxypropyl cellulose, polyvinyl methyl ether, polyvinylpyrrolidone, polyethyloxazoline, starch or cellulose esters, particularly the acetates with a degree of substitution less than 2.5; the latter polymers functioning to increase the water sensitivity of the adhesives which may be desired for some applications.

Other hydrophobic compatible polymers include elastomeric polymers such as styrene containing block copolymers, e.g., styrene-isoprene-styrene, epoxidized polyisoprene, styrene-butadiene-styrene, styrene-ethylene butylene-styrene, styrene-ethylene propylene styrene may also be present at levels up to about 30% by weight. Of these polymers, those based on styrene-isoprene-styrene are most preferred.

Among the applicable stabilizers or antioxidants which may be included herein are high molecular weight hindered phenols and multifunctional phenols such as sulfur and phosphorous-containing phenols. Representative hindered phenols include: 1,3,5-trimethyl-2,4,6-tris(3,5-di-tert-butyl-4-hydroxyphenyl) propionate; n-octadecyl 3,5-di-tert-butyl-4-hydroxyphenyl) propionate; 4,4'-methlenebis (2,6-di-tert-butylphenol); 4,4'-thiobis (6-tert-butyl-o-cresol); 2,6-di-tert-butylphenol; 6-(4-hydroxyphenoxy)-2,4-bis(n-octylthio)-1,3,5-triazine; di-n-octadecyl-3,5-di-tert-butyl-4-hydroxybenzylphosphonate; 2-(n-octylthio)-ethyl 3,5-di-tert-butyl-4-hydroxybenzoate; and sorbitol hexa[3-(3,5-di-tert-butyl-4-hydroxyphenyl)-propionate]. If used, the stabilizer is present in levels of about 0.05 to 3% by weight.

Other optional additives may be incorporated into the hot melt compositions in order to modify certain properties thereof. Among these additives may be included colorants such as titanium dioxide; and fillers such as talc and clay, etc.

Therefore in one embodiment, a hot melt adhesive composition in accordance with the present invention comprises (a) 20 to 80% by weight of a sulfonated polyester; (b) 0 to 35% by weight of a compatible tackifier; (c) 5 to 40% by weight of at least one crystalline material selected from the group consisting of a compatible crystalline wax diluent and a crystalline thermoplastic polymer; (d) 1–30% by weight of an anionic plasticizer; (e) 3 to 30% by weight of a pH adjusting agent, particularly an acidic plasticizer; (f) to 0.05 to 3% by weight of an indicating agent capable of changing color in response to changes in pH; and (g) 0 to 3% by weight of a stabilizer; wherein the total of (a)–(g) equals 100% by weight.

It will be recognized that the general formulation described above can be adapted to include a wide variety of hot melt adhesive compositions, the more precise formulations of which will vary depending upon the specific end use, as known to those skilled in the particular art.

The hot melt adhesive compositions of the invention may be formulated using techniques known in the art. An exemplary procedure for preparing an adhesive of the above embodiment involves placing approximately 40% of the total tackifying resin concentration with all the polymer, wax, plasticizers and stabilizers in a jacketed mixing kettle, preferably in a jacketed heavy duty mixer, which is equipped with rotors and thereupon raising the temperature to a range of from up to about 190° C. After the resin has melted, the temperature is lowered to 150° to 165° C. Mixing and heating are continued until a smooth, homogeneous mass is obtained whereupon the remainder of the tackifying resin is thoroughly and uniformly admixed therewith.

As noted above, the sulfonated polyester containing hydrophilic hot melt adhesives of the invention will be formulated differently depending upon the particular end use. The resultant adhesives may be used in the assembly or construction of various disposable applications including, but not limited to, sanitary napkins, disposable diapers, hospital gowns, bed pads and the like. In particular, adhesives are useful for the construction of disposable articles using multi-line, spray, or slot-coating construction techniques wherein at least one flexible film substrate is bonded to at least one tissue, non-woven, polyolefin or other flexible polymeric film substrate.

With high levels of crystalline polymers, adhesives suitable as films or binder fibers can be prepared. Generally at least 15 and preferably 20 to 40% crystalline polymer is required for these applications. In contrast construction adhesives require a high degree of flexibility, but still need at least 5% of a crystalline polymer to avoid cold flow, preferably 5 to 10%.

In the following illustrative examples all parts are given by weight and all temperatures in degrees Celsius unless otherwise noted.

EXAMPLES

In preparing the following samples, a heavy duty mixer which had been heated to 165° C. and which was equipped with a stirring paddle was charged with 40% of the tackifying resin and/or diluent. After melting of the resins, stirring was then initiated whereupon the polyester was added slowly at 165° C. over a one-half hour period after which the temperature was lowered to 150° C. Heating and stirring were continued until a homogeneous mass was obtained whereupon the remainder of the tackifying resin and/or diluent was admixed therewith.

The samples were tested using the following procedures:

Viscosity measurements were determined after 30 minutes using a Brookfield viscometer (Spindle 27).

Some of the adhesives were also tested for thermal stability by storing at 275° F. for 24 hours. After the testing period, remove the jar, check for the following:
 a. Skin
 b. Dirt/char particles
 c. Sedimentation—partial skin precipitating and falling to the bottom of the jar.
 d. Volatile char
 e. Gelation—carefully examine the contents with a glass stirring rod for signs of gels or lumps.
 f. Color or odor
 g. Product separation—the presence of distinct layers, also known as phasing.

The following were used in the formulations:

EASTMAN AQ 1350 is a branched sulfonated polyester available from Eastman Chemical.

12-hydroxystearic acid from CasChem Inc.

PARICIN 220 is a 12-hydroxystearamide wax from CasChem Inc.

SANTOVAR is a 2,5-di(tert-amyl) hydroquinone antioxidant from Monsanto.

TNPP is a tris nonylphenyl phosphite antioxidant from GE Chemicals.

Isostearic acid from Unichemia.

NIREZ 300 is a phenolic modified terpene having a Ring and Ball softening point about 112° C. and available from Arizona Chemical Company.

PLASTHALL BH-1 is nonionic polyester adipate plasticizer from CP Hall Inc.

FORAL NC is an ionic polar tackifier available from Hercules.

EMULSIFIER K-30, a solid alkane sulfonate available from Bayer Inc.

BROMOCRESOL GREEN, a pH indicating agent form Aldrich Chemical Company.

Example 1

Table 1 shows the formulations of samples tested. Sample I-1 is a control which does not comprise any acid plasticizer (pH adjusting agent) or indicating agent. Sample I-2, also a control, contains indicating agent, but no acid plasticizer. Samples I-3 and I-4 each comprise an acidic plasticizer, isostearic acid. Sample I-4 also contains EMULSIFIER K-30, an anionic plasticizer.

TABLE 1

| | (% by weight) | | | |
|---|---|---|---|---|
| | I-1 | I-2 | I-3 | I-4 |
| EASTMAN AQ 1350 | 60 | 60 | 60 | 60 |
| NIREZ 300 | 10 | 10 | 0 | 0 |
| PARICIN 220 | 15 | 15 | 0 | 0 |
| PLASTHALL BH-1 | 15 | 15 | 0 | 0 |
| Isostearic Acid | 0 | 0 | 10 | 10 |
| 12-hydroxystearic acid | 0 | 0 | 10 | 10 |
| FORAL NC | 0 | 0 | 20 | 15 |
| EMULSIFIER K-30 | 0 | 0 | 0 | 5 |
| SANTOVAR A | 0.5 | 0.5 | 0.5 | 0.5 |
| TNPP | 0.5 | 0.5 | 0.5 | 0.5 |
| Bromocresol Green | 0 | 0.1 | 0.1 | 0.1 |

The results are shown below:

TABLE 2

| | I-1 | I-2 | I-3 | I-4 |
|---|---|---|---|---|
| Viscosity (cps) | | | | |
| 250° F. | 3000 | | 2000 | 2100 |
| 275° F. | 2000 | | 1000 | 1200 |
| 300° F. | 1000 | | 650 | 800 |
| Initial color of hot melt | yellow | Blue-green | Dark orange | Dark orange |
| Color of hot melt after being soaked in water | Yellow | Blue-green | Blue-green | Blue-green |
| Time in seconds of color change | no change in color | no change in color | 45 seconds | 10–15 seconds |
| Thermal Stability 275° F. @ 72 hrs. | | | | |
| Skin/Gel/Edge ring | None | | None | None |
| Char | None | | None | Slight Swirl |
| Odor | Slight | | Present | Present |

TABLE 2-continued

|  | I-1 | I-2 | I-3 | I-4 |
|---|---|---|---|---|
| Color | Dark | | Dark Orange | Orange-Brown |
| Separation | Yellow | | None | None |
| Change Viscosity (%) | None | −30% | −25% | −12% |

The results in Table 2 show that there was no color change with Control Sample I-1, the control, which does not contain any indicating agent. Control Sample I-2, which does contain indicating agent, but no acidic plasticizer, initially changes to a green color and does not change color further upon contact with water. Samples I-3 and I-4, both of which contain isostearic acid, did not initially change color when prepared with the indicating agent, however, upon insult with water the color changed. Here Bromocresol Green was used and the color change was from orange-yellow to blue.

In addition, the above results show that Sample I-4, which contained anionic plasticizer, changed color much more quickly than Sample I-3, which did not contain anionic plasticizer. These results indicate that the presence of the anionic plasticizer accelerates the color change of the indicator.

Example 2

An adhesive formulation was prepared with and without an acidic plasticizer, here isostearic acid. The formulations are shown below:

TABLE 3

| | (% by weight) | |
|---|---|---|
| | II-1 | II-2 |
| EASTMAN AQ 1350 | 60 | 60 |
| Isostearic Acid | 10 | 0 |
| 12-hydroxystearic acid | 10 | 10 |
| FORAL NC | 20 | 20 |
| SANTOVAR A | 0.5 | 0.5 |
| TNPP | 0.5 | 0.5 |
| Bromocresol Green | 0.1 | 0.1 |

Sample II-2 above, prepared without isostearic acid turned green when the indicator, Bromocresol Green, was added. Sample II-1, which included isostearic acid, did not change color when the indicator was added. However Sample II-1 was subsequently contacted with water, which raised the pH of the composition, and activated indicator (turned green). This data shows that the pH adjusting agent, isostearic acid, is necessary to prevent the adhesive form changing color prior to insult with urine or water.

We claim:

1. A wetness indicating sulfonated polyester-based hot melt adhesive composition comprising a sulfonated polyester, a crystalline polar wax, a pH adjusting component and an indicating agent which is capable of changing color in response to changes in pH.

2. A wetness indicating hot melt adhesive according to claim 1 wherein the pH adjusting component is an acidic plasticizer.

3. A wetness indicating hot melt adhesive according to claim 2 wherein the pH adjusting component is an acidic plasticizer with a carboxylic acidic functional group.

4. A wetness indicating hot melt adhesive according to claim 3 wherein the pH adjusting component is selected from the group consisting of isostearic acid, azelaic acid, stearic acid, oleic acid, linoleic acid, ricinoleic acid, dimer acid and combinations thereof.

5. A wetness indicating hot melt adhesive according to claim 1 wherein the indicating agent is an acid-base indicator.

6. A wetness indicating hot melt adhesive according to claim 5 wherein the indicating agent is selected from the group consisting of Ethyl Red, Bromophenol Blue, Bromocresol Green, Bromophenol Blue, and combinations thereof.

7. The wetness indicating hot melt adhesive according to claim 1 wherein the wax is 12-hydroxy stearic acid.

8. A disposable product comprising a wetness indicating sulfonated polyester-based hot melt adhesive composition, said composition comprising a sulfonated polyester, a crystalline polar wax, a pH adjusting component and an indicating agent which is capable of changing color in response to changes in pH.

9. A disposable product according to claim 8 wherein the pH adjusting component is selected from the group consisting of isostearic acid, azelaic acid, stearic acid, oleic acid, linoleic acid, ricinoleic acid, dimer acid and combinations thereof.

10. A disposable product according to claim 8 wherein the indicating agent is selected from the group consisting of Ethyl Red, Bromophenol Blue, Bromocresol Green, Bromophenol Blue, and combinations thereof.

11. A disposable product according to claim 8 wherein the product is a diaper.

12. The wetness indicating hot melt adhesive according to claim 8 wherein the wax is 12-hydroxy stearic acid.

* * * * *